United States Patent
Machida

(10) Patent No.: US 8,706,191 B2
(45) Date of Patent: Apr. 22, 2014

(54) MAGNETIC RESONANCE IMAGING APPARATUS AND MAGNETIC RESONANCE ANGIOGRAPHY METHOD

(75) Inventor: Yoshio Machida, Nasushiobara (JP)

(73) Assignees: Kabushiki Kaisha Toshiba, Minato-Ku, Tokyo (JP); Toshiba Medical Systems Corporation, Otawara-Shi, Tochigi-Ken (JP)

(*) Notice: Subject to any disclaimer, the term of this patent is extended or adjusted under 35 U.S.C. 154(b) by 1375 days.

(21) Appl. No.: 11/667,462

(22) PCT Filed: Oct. 3, 2006

(86) PCT No.: PCT/JP2006/319785
§ 371 (c)(1),
(2), (4) Date: May 10, 2007

(87) PCT Pub. No.: WO2007/040224
PCT Pub. Date: Apr. 12, 2007

(65) Prior Publication Data
US 2008/0009708 A1    Jan. 10, 2008

(30) Foreign Application Priority Data

Oct. 5, 2005    (JP) ................................. 2005-292580

(51) Int. Cl.
*A61B 5/05*    (2006.01)

(52) U.S. Cl.
USPC ........... 600/420; 600/407; 600/410; 600/411; 600/415; 600/419

(58) Field of Classification Search
USPC ................. 600/407, 410, 411, 415, 419, 420; 424/9.1, 9.3; 5/600, 601; 324/307, 309; 382/100, 128, 131
See application file for complete search history.

(56) References Cited

U.S. PATENT DOCUMENTS

| | | | |
|---|---|---|---|
| 4,825,162 A | * | 4/1989 | Roemer et al. ................. 324/318 |
| 5,166,875 A | | 11/1992 | Machida |

(Continued)

FOREIGN PATENT DOCUMENTS

| | | |
|---|---|---|
| EP | 0 654 675 A1 | 5/1995 |
| EP | 1 362 550 A1 | 11/2003 |

(Continued)

OTHER PUBLICATIONS

Kruger et al., "Continuously Moving Table Data Acquisition Method for Long FOV Contrast-Enhanced MRA and Whole-Body MRI," Magnetic Resonance in Medicine 47, 2002, pp. 224-231.

(Continued)

*Primary Examiner* — Tse Chen
*Assistant Examiner* — Jason Ip
(74) *Attorney, Agent, or Firm* — Nixon & Vanderdye PC

(57) ABSTRACT

A magnetic resonance imaging apparatus acquires 3D data of a subject, extracts 2D data for ky=constant out of the 3D data concurrently with the collection of 3D data, Fourier-transforms in a z-axis direction the extracted 2D data for ky=constant and rearranges the same on a kx-z space concurrently with the collecting of 3D data, performs a one-dimensional Fourier transform on z-data completed in a kx direction and acquires a 2D image for real space concurrently with the collection of 3D data, and displays a 2D image on a monitor concurrently with the collection of 3D data. Meanwhile, the the 3D data in the z-axis direction is Fourier-transformed and rearranged on a kx-ky-z space, a two-dimensional Fourier transform is performed on the z-data completed in a kx/ky direction and a 3D image is acquired for real space.

20 Claims, 11 Drawing Sheets

(56) References Cited

U.S. PATENT DOCUMENTS

| | | | |
|---|---|---|---|
| 5,631,560 A | | 5/1997 | Machida |
| 5,713,358 A | * | 2/1998 | Mistretta et al. ............. 600/420 |
| 6,912,415 B2 | | 6/2005 | Kruger et al. |
| 2002/0021128 A1 | * | 2/2002 | Kuhara .......................... 324/309 |
| 2002/0173715 A1 | | 11/2002 | Kruger et al. |
| 2003/0120151 A1 | * | 6/2003 | Constantinides ............. 600/431 |
| 2003/0214295 A1 | * | 11/2003 | Polzin et al. .................. 324/309 |
| 2006/0020198 A1 | | 1/2006 | Riederer et al. |

FOREIGN PATENT DOCUMENTS

| | | |
|---|---|---|
| JP | 3146034 B2 | 1/2001 |
| WO | 2004/081597 A1 | 9/2004 |

OTHER PUBLICATIONS

Zhu et al., "Extended Field-of-View Imaging with Table Translation and Frequency Sweeping," Magnetic Resonance in Medicine 49, 2003, pp. 1106-1112.

Kannengiesser, "Parallel Imaging for Continuously Moving Table MRI Using Moving RF Coils and In-Place Sensitivity Calibration," 2nd International Workshop on P-MRI, 2004, p. 40.

Zenge et al., "MR Imaging with a Continuously Rolling Table Platform and High-Precision Position Feedback," Proc. Intl. Soc. Mag. Reson. Med. 11, 2004, p. 2381.

Ookawa et al., "One-Second Temporal Resolution 4D MR DSA with 3D TRICKS, Elliptical Centric View Ordering, and Parallel Imaging," Proc. Intl. Soc. Mag. Reson. Med. 11, 2003, pp. 324.

International Search Report of PCT/JP2006/319785, mailed Jan. 9, 2007.

Keupp et al., "Continuous Moving Table SENSE Imaging", Proc. Int'l. Soc. Mag. Reson. Med. 11, 2004, p. 324.

Polzin et al., "Correction for Gradient Field Distortions in Moving Table Imaging", Proc. Intl. Soc. Mag. Reson. Med. 10, 2002, p. 380.

Bernstein et al., "Handbook of MRI Pulse Sequences", Elsevier Academic Press, Sep. 21, 2004, pp. 357-358, ISBN 978-0-12-092861-3.

Sabati et al., "Space-time relationship in continuously moving table method for large FOV peripheral contrast-enhanced magnetic resonance angiography", Physics in Medicine & Biology, Sep. 2003, vol. 48, No. 17, pp. 2739-2752.

Hu et al., "Application of Variable FOV to Continuously Moving Table MRI", Proc. Int'l. Soc. Mag. Reson. Med. 11, Jul. 2003, p. 1073.

Kruger et al., "A Dual-Velocity Acquisition Method for Continuously-Moving-Table contrast-Enhanced MRA", Proc. Int'l. Soc. Mag. Reson. Med. 11, 2004, p. 233.

Supplementary European Search Report dated Jan. 29, 2010 in EP 06821814.8.

English translation of the International Preliminary Report on Patentability dated Sep. 9, 2008 in PCT/JP2006/319785.

Kunihiro Watanabe, et al., "Evaluation of Three-dimensional Contrast-enhanced MRA Using Differential Rate K-space Sampling (DRKS)," *Japanese Society Radiological Technology*, 58(12), pp. 1609-1614 (2002).

Office Action dated Oct. 2, 2012, in JP 2006-270793.

J. Keupp, et al., "Continuous Moving Table SENSE Imaging," *Proc. Intl. Soc. Mag. Reson. Med.*, vol. 12, p. 324 (2004).

* cited by examiner

MAGNETIC RESONANCE IMAGING APPARATUS AND MAGNETIC RESONANCE ANGIOGRAPHY METHOD

This application is the US national phase of international application PCT/JP2006/319785, filed 3 Oct. 2006, which designated the U.S. and claims priority of JP 2005-292580, filed 5 Oct. 2005, the entire contents of each of which are hereby incorporated by reference.

TECHNICAL FIELD

The present exemplary embodiments relate to an art that obtains an image of a subject at a field of view while continuously moving the table top having placed thereon a subject, and more particularly to a magnetic resonance imaging apparatus and magnetic resonance angiography method adapted to move the table top in a manner following the velocity of blood flow.

BACKGROUND ART

The medical imaging apparatus is to provide a great deal of information about a subject through images, which plays an important role in many medical actions including disease diagnosis, medical treatment and surgical planning. At present, the major medical imaging apparatuses include ultrasonic diagnostic apparatuses, CT (computerized tomography) apparatuses, MRI (magnetic resonance imaging) apparatuses and nuclear medical diagnostic apparatuses. Among those, the magnetic resonance imaging apparatus is capable of acquiring images excellent in contrast for soft tissue, thus occupying an important position in the medical imaging diagnosis.

Imaging speed has advanced for the magnetic resonance imaging apparatus, allowing for taking successive images of three-dimensional data. Meanwhile, there is developed an art to take an image while moving a table top, enabling imaging over a broad range. Besides the intermittent imaging with the alternate repetition of imaging and movement, imaging is recently available with table-top continuous movement in X-ray CT. The three-dimensional imaging with table-top continuous movement is suitably applied in MRA (magnetic resonance angiography) with a contrast agent.

Meanwhile, there is a PI (parallel imaging) technique as one of high-speed imaging techniques based on the magnetic resonance imaging apparatuses. The PI technique captures images using an RF (radio frequency) coil that is structured as a multi-coil with a plurality of surface coils so that an NMR (nuclear magnetic resonance) signal can be received simultaneously at the surface coils and used in reconstructing an image.

With the PI technique, imaging time is to be reduced because the phase encode count (times) required for data acquisition for use in image reconstruction can be reduced by a factor corresponding to the number of surface coils. The PI technique is applicable together with 3D imaging and hence improved further in its performance.

Because a great deal of data processing is required for acquisition of data in a series of high-speed great-capacity imaging with traditional magnetic resonance imaging apparatus, there is difficulty in producing a three-dimensional image concurrent with data acquisition. For simple three-dimensional imaging, there is proposed a method to produce a two-dimensional image corresponding to a projection image, which is used as a monitor for an imaging result.

However, such a method has not been proposed for three-dimensional imaging with continuous table-top movement.

Furthermore, where angiography is conducted on a subject by means of conventional magnetic resonance imaging apparatus using a contrast agent, there is a difficulty in setting up the table top in a position to follow the flow velocity of the contrast agent, and hence a difficulty in taking an image in a region within a field-of-view in a manner to follow the flow velocity of the contrast agent. This is because the flow velocity of the contrast agent differs from subject to subject and from region to region even on the same subject and thus, because of such broad possible ranges, table-top movement is not done at the contrast agent flow velocity. Consequently, data obtained by means of traditional magnetic resonance imaging apparatus often does not follow the contrast agent flow velocity and hence is not ideally suited for use in diagnosis.

Prior art documents related to the present application include the following.
Patent document 1: U.S. Pat. No. 5,631,560 description
Patent document 2: U.S. Pat. No. 5,166,875 description
Patent document 3: Japanese Patent No. 3,146,034
Patent document 4: U.S. Patent Application Publication No. 2006/0020198
Patent document 5: U.S. Pat. No. 6,912,415 description
Non-patent document 1: M. Sabati, M. L. Lauzon and R. Frayne; "Space-time relationship in continuously moving table method for large FOV peripheral contrast-enhanced magnetic resonance angiography*"; Phys Med Biol 2003 48: pages 2739-2752
Non-patent document 2: David G. Kruger, Stephen J. Riederer, Roger C. Grimm, and Phillip J. Rossman; "Continuously Moving Table Data Acquisition Method for Long FOV Contrast-Enhanced MRA and Whole-Body MRI"; Magnetic Resonance in Medicine 47: pages 224-231 (2002)
Non-patent Document 3: Yudong Zhu and Charles L. Dumoulin; "Extended Field-of-View Imaging With Table Translation and Frequency Sweeping"; Magnetic Resonance in Medicine 49: pages 1106-1112 (2003)
Non-patent Document 4: Stephan A. R. K.; "Parallel Imaging Continuously Moving Table MRI Using Moving RF Coils and In-place Sensitivity Calibration"; 2nd international work shop on P-MRI: 2004: page
Non-patent Document 5: M. O. Zenge, H. H. Quick, F. M. Vogt, M. E. Ladd; "MR Imaging with a Continuously Rolling Table Platform and High-Precision Position Feedback"; IS MRM 2004: page 2381
Non-patent Document 6: M. Ookawa, N. Ichinose, M. Miyazaki, I. Miyazaki, S. Sugiura; "One-Second Temporal Resolution 4D MR DSA with 3D TRICKS, Elliptical Centric View Ordering, and Parallel Imaging"; ISMRM 2003: page 324 (2003).

BRIEF SUMMARY

The present exemplary embodiments, made in view of the above circumstance, aim to provide a magnetic resonance imaging apparatus and magnetic resonance angiography method that can control the movement rate of a table top while observing the actual flow of a contrast agent, thus obtaining image data following the flow velocity of the contrast agent.

In order to solve the foregoing problem, a magnetic resonance imaging apparatus according to an exemplary embodiment may comprise a magnetic resonance imaging apparatus having a table top for resting a subject thereon, a table-top drive mechanism for moving the table top in a lengthwise direction (z-axis direction), and a computer for controlling a movement rate of the table top by providing a control signal to the table-top drive mechanism, so that the subject can be taken an image while continuously moving the table top, the apparatus comprising: table-top movement-rate control means that controls the table-top drive mechanism to move the table top; data acquiring means that acquires 3D data constituted by a nuclear magnetic resonance signal while moving the table top; 2D-image acquiring means that acquires 2D image depending upon 2D data forming a part of the 3D data acquired by the data acquiring means, concurrently with acquiring of the 3D data by the data acquiring means; and display control means that causes to display the 2D image, concurrently with acquiring of the 3D data by the data acquiring means.

In order to solve the foregoing problem, a magnetic resonance imaging apparatus according to an exemplary embodiment may comprise a magnetic resonance imaging apparatus having a table top for resting a subject thereon, a table-top drive mechanism for moving the table top, and a computer for controlling a movement rate of the table top by providing a control signal to the table-top drive mechanism, so that the subject can be taken an image while continuously moving the table top by injecting a contrast agent to a blood vessel interior of the subject thereby imaging a temporal movement of the contrast agent, the apparatus comprising: data acquiring means that acquires 3D data formed of a nuclear magnetic resonance signal including a signal that blood flow is emphasized of the subject while moving the table top; 2D-image acquiring means that acquires 2D image based upon 2D data forming a part of the 3D data acquired by the data acquiring means, concurrently with acquiring of the 3D data by the data acquiring means; display control means that causes to display the 2D image, concurrently with acquiring of the 3D data by the data acquiring means; 3D-image acquiring means that acquires 3D image based upon the 3D data; and table-top movement-rate control means that calculates the movement rate according to a rate-change signal inputted and causes the table top to move at the movement rate calculated, concurrently with acquiring of the 3D data by the data acquiring means.

In order to solve the foregoing problem, a magnetic resonance angiography method according to an exemplary embodiment may comprise a magnetic resonance angiography method that takes an image of a subject while continuously moving a table top by injecting a contrast agent in a blood vessel interior of the subject and imaging a temporal movement of the contrast agent, the method comprising: a table-top moving step that moves the table top; a data acquiring step that acquires 3D data constituted by a nuclear magnetic resonance signal including a signal blood flow is emphasized of the subject while moving the table top; a 2D-image acquiring step that acquires a 2D image based upon 2D data forming a part of the 3D data, concurrently with acquiring of the 3D data; a 2D-image display step that displays the 2D image, concurrently with acquiring of the 3D data; a 3D-image acquiring step that acquires a 3D image based on the 3D data; and a movement-rate calculating step that calculates the movement rate according to a rate-change signal inputted, concurrently with acquiring of the 3D data; thereby moving the table top at the movement rate calculated.

In order to solve the foregoing problem, a magnetic resonance angiography method according to an exemplary embodiment may comprise a magnetic resonance angiography method comprising: a table-top moving step that moves in a z-axis direction a table top for resting a subject thereon; a data acquiring step that causes a magnetic resonance excitation in a 3D region of the subject while continuously moving the table top and acquires 3D data constituted by a 3D nuclear magnetic resonance signal from the 3D region; a 2D-image acquiring step that acquires 2D data forming a part of the 3D data, concurrently with acquiring of the 3D data; a 2D-image reconstructing step that performs an image producing process based on the 2D data and produces a 2D image, concurrently with acquiring of the 3D data; and a 2D-mage display step that displays the 2D image, concurrently with acquiring of the 3D data; wherein, each time new 3D data is acquired at the data acquiring step, repeated are the 2D-data acquiring step, the 2D-image reconstructing step and the 2D-image display process to thereby update/display the 2D image by the 2D-image display step.

With the magnetic resonance imaging apparatus and magnetic resonance angiography method according to the invention, the movement rate of the table top can be controlled while observing the actual blood flow velocity interior of a subject, thus obtaining proper image data following the blood flow velocity that is different on a subject-by-subject basis or on a site-by-site basis even in the same subject.

DETAILED DESCRIPTION OF EXEMPLARY EMBODIMENTS

With reference to the drawings, explanation will be made on an embodiment of a magnetic resonance imaging apparatus and magnetic resonance angiography method according to the present invention.

Figure 1:
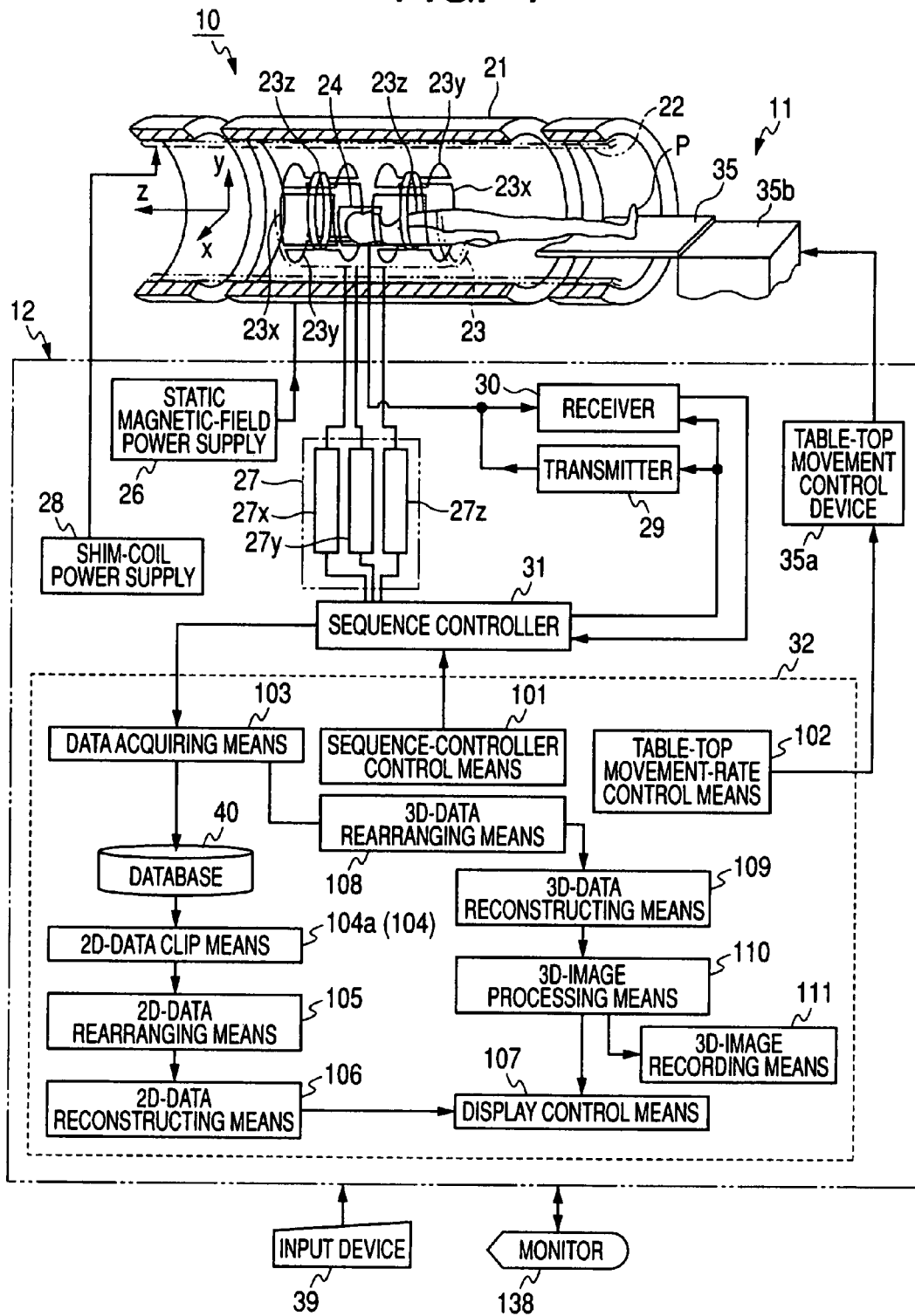
FIG. 1: A schematic diagram showing an embodiment of a magnetic resonance imaging apparatus according to the present invention.

FIG. 1 is a schematic view showing an embodiment of a magnetic resonance imaging apparatus according to the invention.

FIG. 1 shows a magnetic resonance imaging (MRI) apparatus 10 that makes an image of a contrast agent in temporal movement by injecting the contrast agent into an blood vessel interior of a subject and taking an image of the subject while continuously moving a table top resting the subject thereon longitudinally (in a z-axis direction). The magnetic resonance imaging apparatus 10 is constructed with an imaging system 11 and a control system 12.

The imaging system 11 of the magnetic resonance imaging apparatus 10 has a gantry (not shown) provided therein with a static magnetic-field magnet 21, a cylindrical shim coil 22 at an inside of the static magnetic-field magnet 21 and coaxial to the static magnetic-field magnet 21, a gradient magnetic-field coil unit 23 formed at an inside of the static magnetic-field magnet 21 and cylindrical in form, and an RF coil 24 for transmitting an RF (radio frequency) signal at a Larmor frequency (resonance frequency).

Meanwhile, the control system 12 of the magnetic resonance imaging apparatus 10 is provided with a static magnetic-field power supply 26, a gradient magnetic-field power supply 27, a shim-coil power supply 28, a transmitter 29, a receiver 30, a sequence controller (sequencer) 31 and a computer 32.

The static magnetic-field magnet 21 is connected to the static magnetic-field power supply 26. The static magnetic-field magnet 21 is to form a static magnetic field in a field-of-view (FOV) by means of the current supplied from the static magnetic-field power supply 26.

The shim coil 22 is connected to the shim-coil power supply 28 so that a current can be supplied from the shim-coil power supply 28 to the shim coil 22 thereby making a static magnetic field uniform.

The gradient magnetic-field coil unit 23 is made up with an x-axis gradient magnetic-field coil 23$x$, a y-axis gradient magnetic-field coil 23$y$ and a z-axis gradient magnetic-field coil 23$z$. Meanwhile, a table top 35 is provided at an inside of the gradient magnetic-field coil unit 23 so that a subject P can be rested in a recumbent posture on the table top 35. The table top 35 is to be moved axially of the subject P by the table-top drive mechanism 35$b$.

Meanwhile, the gradient magnetic-field coil unit 23 is connected to the gradient magnetic-field power supply 27. The x-axis, y-axis and z-axis gradient magnetic-field coils 23$x$, 23$y$, 23$z$ of the gradient magnetic-field coil unit 23 are respectively connected to x-axis, y-axis and z-axis gradient magnetic-field power supplies 27$x$, 27$y$, 27$z$ of the gradient magnetic-field power supply 27.

By the currents respectively supplied from the x-axis, y-axis and z-axis gradient magnetic-field power supplies 27$x$, 27$y$, 27$x$ to the x-axis, y-axis and z-axis gradient magnetic-field coils 23$x$, 23$y$, 23$z$, gradient magnetic fields x-axis, y-axis and z-axis directions are formed in the field-of-view.

The RF coil 24 is connected to the transmitter 29 and to the receiver 30. The RF coil 24 is made as a multi-coil structured with a plurality of surface coils at least in the z-axis direction. For example, the RF coil 24 is made as a multi-coil structured with surface coils whose four elements are in the x-axis direction, four elements are in the y-axis direction and 10 elements are in the z-axis direction. From now on, explanation is made on the case using a parallel imaging (PI) technique that is an imaging scheme to reconstruct an image by receiving nuclear magnetic resonance (NMR) signals simultaneously at the surface coils, which however is not limitative. The RF coil 24 is to receive an RF signal from the transmitter 29 and transmit an RF magnetic-field pulse to the subject P wherein it receives an NMR signal generated by RF signal excitation due to nuclear spins at the interior of the subject P and provides it to the receiver 30. Incidentally, the RF coil 24 may be provided on the table plate 35 or in the neighborhood of the subject P instead of being built in the gantry.

The sequence controller 31 is connected to the gradient magnetic-field power supply 27, transmitter 29 and receiver 30. The sequence controller 31 has a not-shown CPU (central processing unit) and memory, to store therein sequence information describing control information required to drive the gradient magnetic-field power supply 27, transmitter 29 and receiver 30, e.g. operation control information of the intensity, application time and application timing of a pulse current to be applied to the gradient magnetic-field power supply 27. Meanwhile, the sequence controller 31 is to drive the gradient magnetic-field power supply 27, transmitter 29 and receiver 30 according to a predetermined sequence stored, thereby generating x-axis, y-axis and z-axis gradient magnetic fields as well as an RF signal.

The transmitter 29 is to provide an RF signal to the RF coil 24 depending upon the control information received from the sequence controller 31. Meanwhile, the receiver 30 is to perform a required signal processing on the NMR signal received from the RF coil 24 and an A/D (analog/digital) conversion thereon, thereby producing from the receiver 30 raw data that is a digitized NMR signal. Meanwhile, it provides the produced raw data to the sequence controller 31. The sequence controller 31 receives the raw data from the receiver 30 and provides it to the computer 32.

The computer 32 is assumed configured with computer basic hardware including a not-shown CPU and ROM (read only memory), an internal memory RAM (random access memory) and an external memory HD (hard disk). Meanwhile, the computer 32 is connected with a monitor 38 that displays a real time two-dimensional (2D) angiographic image for reference, a three-dimensional (3D) angiographic image for diagnosis, various parameters and a rate-change signal input screen referred later, and an input device 39, such as a mouse or a joystick, allowing for user's operation to provide an operation command together with PI-sequence select information and input rate-change signal for the table top 35. Incidentally, the computer 32, in a certain case, has a drive to read various application programs and data from a media storing various application programs and data.

The CPU is a control section taking control of computer 32 overall, to execute the various control programs and application programs stored in the ROM and HD and perform control of the computer 32 and of communications, data acquisition, editing and so on. It has, as a control program, a program for utilization of a GUI (graphical user interface) capable of basic operations by means of the input device 39 through use of a graphic on the display screen.

The ROM is a nonvolatile storage device to store a BIOS (basic input/output system) mainly as a control program for the computer 32 or data. The RAM is a nonvolatile storage device for use as a CPU work memory or in temporary storage. Incidentally, the ROM may be a mask ROM in a type not to be rewritten or a PROM (programmable ROM) in a type to be rewritten.

The HD is a storage device that stores various application programs and data. A database 40, that forms a kx-z and kx-xy-z hybrid spaces for arranging thereon the raw data acquired from the imaging system 11, is stored in the internal memory or the external storage device. In the figure, the HD is described as a typical example. Meanwhile, in the following description, storage in the HD is assumed described as one example. Incidentally, the hybrid space is a space that a Fourier space (k space) and a real space are combined together.

By reading and executing a program by means of the CPU, the computer 32 is to function as sequence-controller control means 101, table-top movement-rate control means 102, data acquiring means 103, 2D-data acquiring means 104, 2D-data rearranging means 105, 2D-image reconstructing means 106, display control means 107, 3D-data rearranging means 108, 3D-image reconstructing means 109, 3D-image processing means 110 and 3D-image recording means 111. Incidentally, the computer 32 may be configured by providing particular hardware (circuit) instead of resorting to a program.

The sequence-controller control means 101 has a function to perform a 3D scanning by providing a required sequence to the sequence controller 31 depending upon the information of from the input device 39 or other element.

The table-top movement-rate control means 102 has a function to calculate a movement rate of the table top 35 according to the input of a rate-change signal for the table top 35 inputted by the input means 39 concurrently with the acquiring of 3D raw data by the data acquiring means 103 referred later, and to control the table-top drive mechanism 35b through a table-top movement control device 35a in a manner moving the table top 35 at the movement rate.

The data acquiring means 103 has a function to acquire the 3D raw data collected by performing the 3D scanning.

The 2D-data acquiring means 104 has a function to acquire 2D data, related to ky which "ky=constant", as a part of the 3D raw data acquired by the data acquiring means 103, concurrently with the acquiring of 3D raw data by the data acquiring means 103. More specifically, 2D-data acquire means 104a, as the 2D-data acquiring means, has a function to extract 2D data, related to ky which "ky=constant", out of the 3D raw data acquired by the data acquiring means 103, concurrently with the acquiring of 3D raw data by the data acquiring means 103. Incidentally, the 2D-data acquiring means 104 may select 2D data, related to ky which "ky=constant", out of the 3D raw data acquired by the data acquiring means 103, concurrently with the acquiring of 3D raw data by the data acquiring means 103.

The 2D-data rearranging means 105 has a function to Fourier-transform, in the z-axis direction, the 2D data for "ky=0" extracted by the 2D-data extract means 104a, concurrently with the acquiring of 3D raw data by the data acquiring means 103, and to rearrange it on the kx-z hybrid space.

The 2D-image reconstructing means 106 has a function to perform a one-dimensional Fourier-conversion on the z-data completed in the ky direction by the 2D-data rearranging means 105, concurrently with the acquiring of 3D raw data by the data acquiring means 103, and to acquire a 2D image (projection image) for a real space.

The display control means 107 has a function to display an angiographic image as a 2D projection image on the monitor 38 by providing the monitor 38 with the image data obtained by the 2D-reconstruction at the 2D-image reconstructing means 106, concurrently with the acquiring of 3D raw data by the data acquiring means 103.

The 3D-data rearranging means 108 has a function to Fourier-transform, in the z-axis direction, the 3D raw data acquired by the data acquiring means 103 and to rearrange it on the kx-ky-z hybrid space.

The 3D-image reconstructing means 109 has a function to perform a two-dimensional Fourier transform on the z-data completed in the kx/ky direction by the 3D-data rearranging means 108 and to acquire a 3D image for a real space.

The 3D-image processing means 110 has a function to acquire a 3D projection image by performing an SVR (shaded volume rendering) processing, an MaxIP (maximum intensity projection) processing and MinIP (minimum intensity projection) processing on the 3D image acquired by the 3D-image reconstructing means 109, and a function to perform an image processing, such as MPR (multiple plane rendering) processing.

The 3D-image recording means 111 has a function to record, onto the HD, the 3D projection image acquired at the 3D-image processing means 110. Meanwhile, the 3D projection image may be configured in a manner to be displayed on the monitor 38 through the display control means 107.

Figure 2:
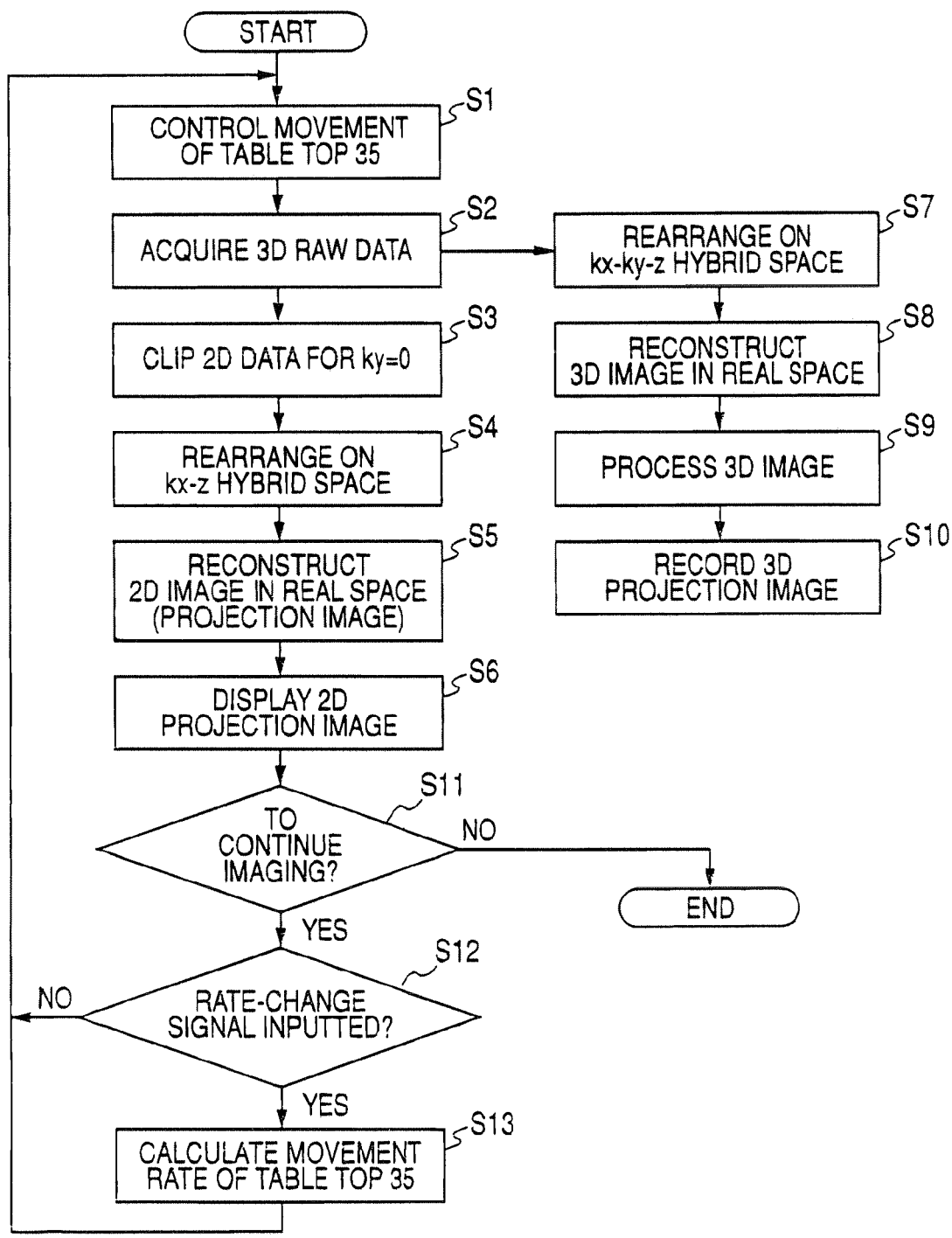
FIG. 2: A flowchart showing a magnetic resonance imaging method according to the invention.

Using the flow chart shown in FIG. 2, explanation is next made of a magnetic resonance imaging method according to an exemplary embodiment.

A subject P is placed in a recumbent posture on the table top 35. Simultaneously, a current is supplied from the static magnetic-field power supply 26 to the static magnetic-field magnet 21, to form a static magnetic field at the inside of the static magnetic-field magnet 21. Meanwhile, a current is supplied from the shim-coil power supply 28 to the shim coil 22, to make uniform the static magnetic field formed in a field-of-view.

An operation command is provided, together with PI-sequence select information, from the input device 39 to the sequence-controller control means 101. Consequently, the sequence-controller control means 101 provides a PI sequence to the sequence controller 31. The sequence controller 31 drives the gradient magnetic-field power supply 27, transmitter 29 and receiver 30 according to the PI sequence received from the sequence-controller control means 101, to thereby form x-axis, y-axis and z-axis gradient magnetic fields in the field-of-view and generate an RF signal.

On this occasion, the x-axis, y-axis and z-axis gradient magnetic fields, formed by the gradient magnetic-field coil, are used mainly as a phase-encoding (PE) gradient magnetic field, a readout (RO) gradient magnetic field and a slice-encoding (SE) gradient magnetic field, respectively. Consequently, there appears a regularity in the rotating direction of the nuclear spins interior of the subject P. The two-dimensional positional information, x and y coordinates, formed in the z-direction on a slice by means of the SE ingredient magnetic field, is converted into phase-change and frequency-change amounts of the nuclear spins interior of the subject P by means of the PE and RO gradient magnetic fields.

The transmitter 29 provides an RF signal to the surface coils 24a through respective channels of the RF coil 24, according to the PI sequence. The RF signal is transmitted from the surface coils 24a to the subject P resting upon the table top 35. Furthermore, the NMR signal, caused within the subject P by the magnetic resonance of nuclei contained in the slice according to an RF signal frequency, is received at the surface coils 24a of the RF coil 24 and provided to the receiver 30.

Meanwhile, the table-top movement-rate control means 102 controls the table-top drive mechanism 35b through the table-top movement-control device 35a, thereby moving continuously the table top 35 resting thereon the subject P in the z-direction (step S1).

Receiving the NMR signal from the surface coils 24a of the RF coil 24, the receiver 30 performs various signal processes, including pre-amplification, intermediate-frequency conversion, phase detection, low-frequency amplification and filtering thereon. Furthermore, the receiver 30 performs an A/D conversion on the NMR signal to thereby produce 3D raw data that is a digital-data NMR signal. The receiver 30 provides the produced 3D raw data to the sequence controller 31.

The sequence controller 31 provides the 3D raw data, received from the receiver 30, to the data acquiring means 103 of the computer 32. In the data acquiring means 103, the 3D raw data is acquired (step S2). Namely, the data acquiring means 103 causes a magnetic resonance excitation in a 3D region of the subject P while continuously moving the table top 35. Simultaneously, it acquires 3D raw data constituted by a 3D nuclear magnetic resonance signal from the 3D region.

Then, the 2D-data acquiring means 104 acquires 2D data, related to ky which "ky=constant", which 2D data is a part of the 3D data acquired at step S2, concurrently with the acquiring of 3D raw data at the step S2. More specifically, the 2D-data extract means 104a, as the 2D-data acquiring means 104, extracts 2D data, related to ky which "ky=constant", out of the 3D raw data acquired at the step S2, concurrently with the acquiring of 3D raw data at the step S2 (step S3).

Figure 3:
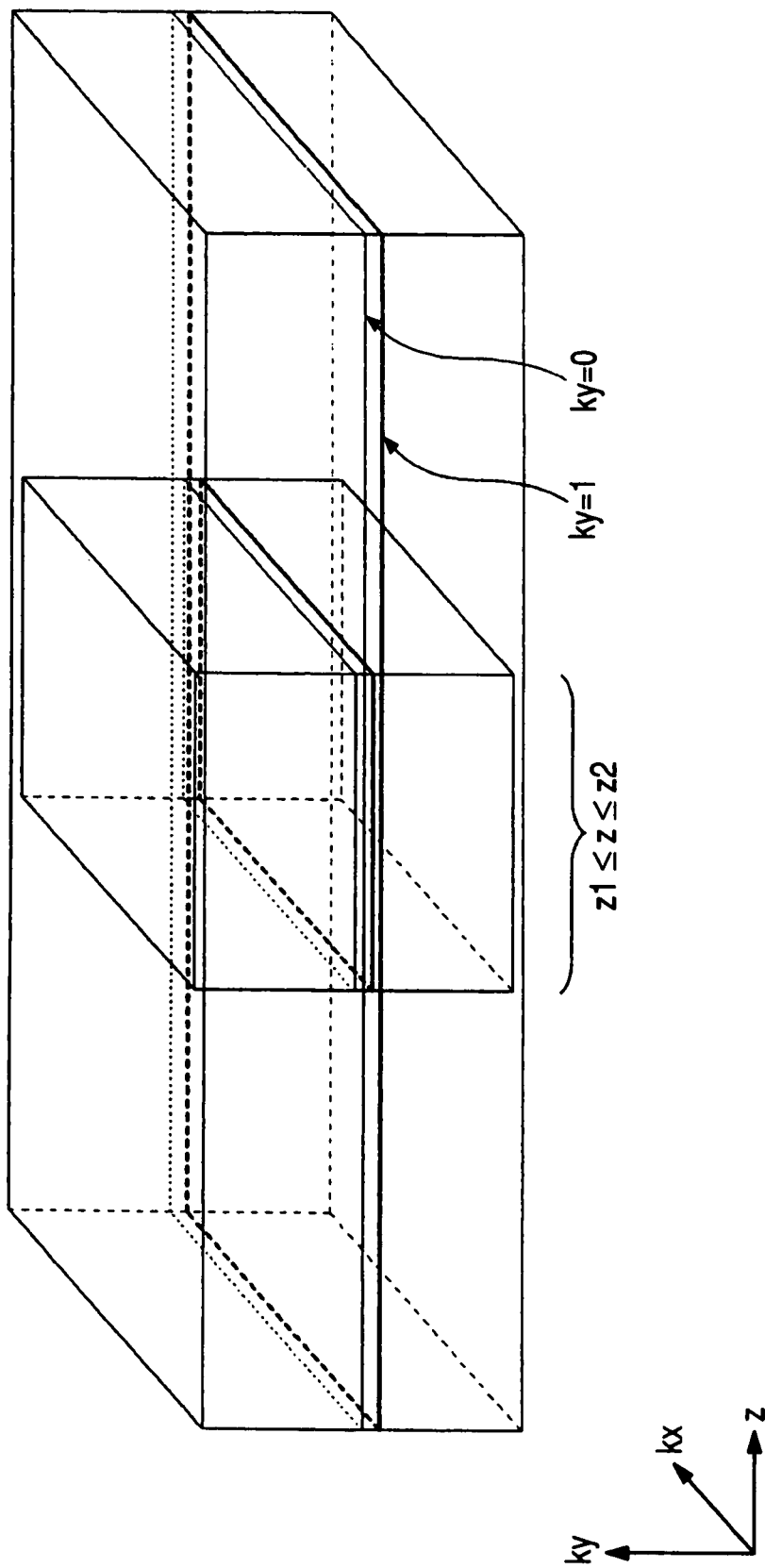
FIG. 3: A figure showing a kx-ky-z hybrid space.

The 2D-data rearranging means 105 Fourier-transforms the 2D data, related to ky which "ky=constant", say a ky for "ky=0", extracted at the step S3, as shown in FIG. 3, in the z-axis direction and rearranges it in a hybrid space kx-z (z1≤z≤z2) formed in the database 40 (step S4). As a result, the 3D raw data changing chronologically is stored, as the database 40, in the HD. FIG. 3 shows a figure showing a kx-ky-z hybrid space wherein the data in z1≤z≤z2, if taken, provides the usual data (projection image) in an amount of one screen. Incidentally, the ky which "ky=constant" is not limited to the case of "ky=0". For example, as shown in FIG. 3, the equivalent result to the case of "ky=0" is obtainable even in the case of "ky=1". Meanwhile, although not shown, the result obtainable is similar to the case of "ky=0" even in the case of "ky=2", "ky=3" or the like.

Figure 4:
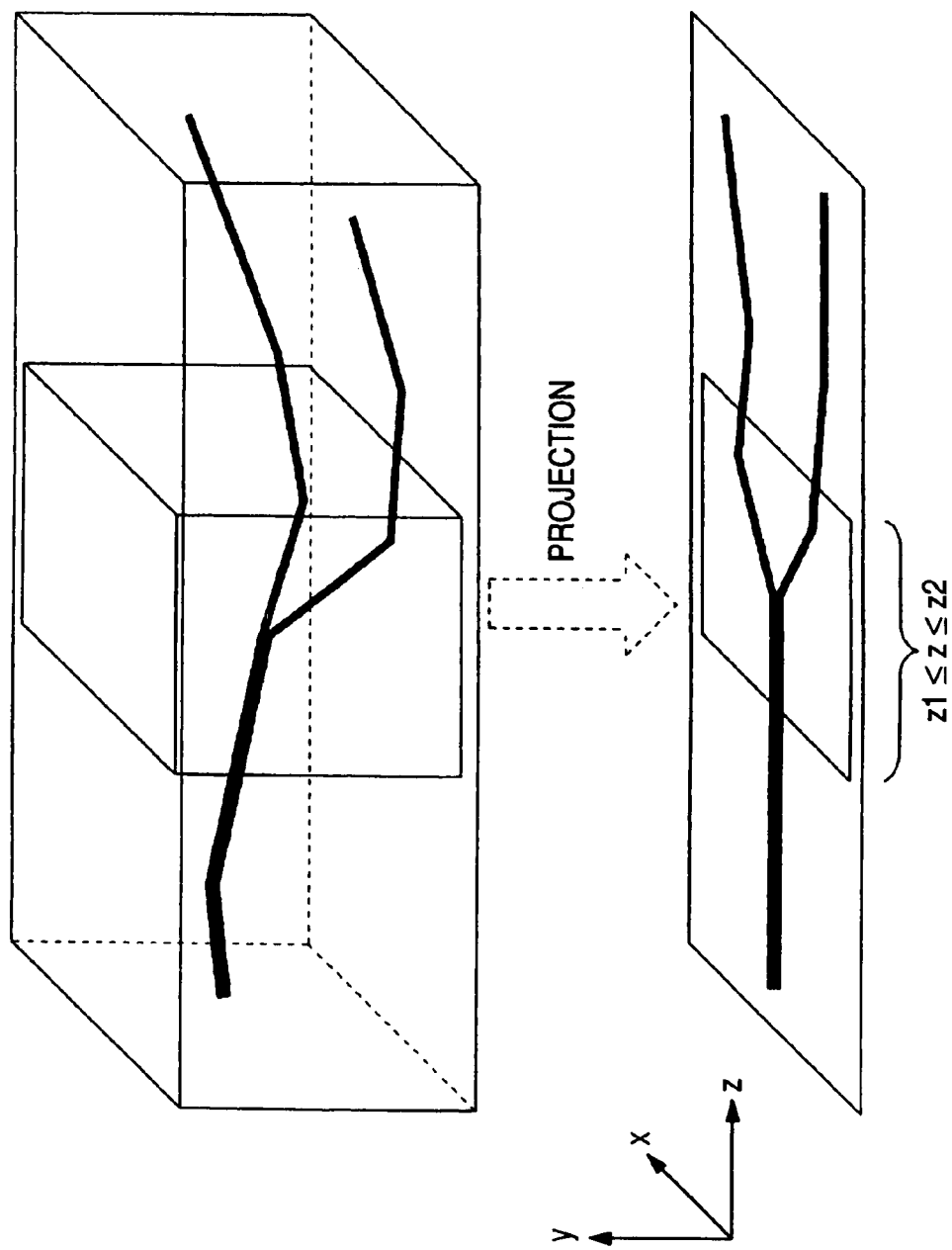
FIG. 4: A figure showing a real space x-y-z corresponding to the kx-ky-z hybrid space.

Then, as shown in FIG. 4, the 2d-image reconstructing means 106 performs a one-dimensional Fourier-transform on the z-data completed in the kx direction and rearranged at the step S4 concurrently with the acquiring of 3D raw data at the step S2, to thereby reconstruct an angiographic image as a 2D image (projection image) for an x-y-z (z1≤z≤z2) space (step S5). FIG. 4 is a figure showing a real space x-y-z corresponding to the kx-ky-z hybrid space shown in FIG. 3, wherein a 2D image is obtainable as a projection image in the range z1≤z≤z2 on the real space. Here, there is shown an angiographic image as an example in the main application.

The display control means 107 shown in FIG. 1 provides the image data reconstructed at the step S5 to the monitor 38 concurrently with the acquiring of 3D raw data at the step S2, and causes the monitor 38 to display an angiographic image as a 2D image thereon (step S6). Therefore, the contrast agent entering the subject P can be observed in real time while sliding the projection data at "k=0", "z1≤z≤z2".

Description is now made on the processing of 3D data that is all the data acquired so far, as a flow of steps S7-S10. There is difficulty in performing the processing of 3D data concurrently with data acquiring, as described in the background art description. The 3D-data rearranging means 108 Fourier-transforms in the z-axis direction the 3D raw data acquired at the step S2, and rearranges it on the kx-ky-z hybrid space formed in the database 40 (step S7). As a result, the 3D raw data chronologically changing is stored as a database 40 on the HD.

The 3D-image reconstructing means 109 performs a two-dimensional Fourier-transform on the z-data completed in the kx/ky direction at the step S7 and reconstructs a 3D image for an x-y-z real space (step S8).

The 3D-image processing means 110 performs an image processing, such as of SVR, MaxIP, MinIP or MPR, on the 3D image acquired at the step S8, and acquires a 3D projection image (step S9).

The 3D-image recording means 111 records the 3D projection image, acquired at the step S9, on the HD (step S10).

Meanwhile, the 3D projection image may be displayed on the monitor 38 through the display control means 107.

Those processes on the 3D data are usually performed later than the progress of data acquiring or after completing the data collection, as mentioned before.

Referring back to the continuation from the step S6, description will be made in detail in the following. Following the step S6, determination is made as to whether or not to continue the imaging of the subject P (step S11). When determined Yes, i.e. to determine the imaging, at the step S11, determination is made whether or not a rate-change signal was inputted to the table-top movement-rate control means 102 by use of the input device 39 (step S12). The user operates the input device 39 as required and inputs a rate-change signal in desired timing to the computer 32. When determined Yes at step S12, i.e. when determined that a rate-change signal was inputted to the table-top movement-rate control means 102 by use of the input device 39, the table-top movement-rate control means 102 calculates a movement rate of the table top 35 (step S13).

Then, the table-top movement-rate control means 102 controls the table-top drive mechanism 35b through the table-top movement control device 35a. The table top 35 is moved at a movement rate calculated at the step S13 (step S1). At the movement rate, 3D raw data is acquired again (step S2). Meanwhile, when determined No at the step S12, i.e. when determined that no rate-change signal was inputted to the computer 32 by use of the input device 39, the table-top movement-rate control means 102 controls the table-top drive mechanism 35b through the table-top movement control device 35a thereby moving the top plate 35 at a movement rate without a change (step S1). Again, 3D raw data is acquired (step S2).

Meanwhile, when determined No at the step S11, i.e. when determined not to continue the imaging, the operation is terminated.

As described above, a 2D projection image can be acquired/displayed continuously by user's input of a rate-change signal as required while viewing a 2D image displayed at the step S6 and acquiring 3D raw data through repeated imaging at a movement rate of the table top 35 calculated at the step S13. Meanwhile, a proper 3D projection image can be continuously acquired by acquiring 3D raw data through repeating the imaging of the table top 35 at a movement rate calculated at the step S13.

Figure 5:
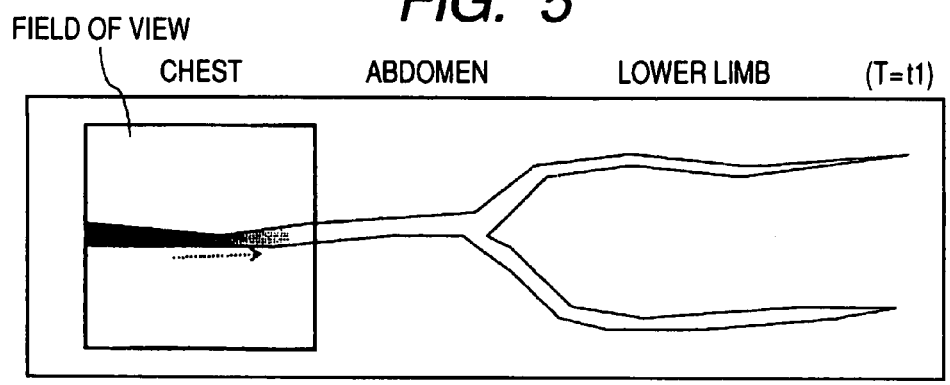
FIG. 5: A figure simulating an angiographic image that is a 2D image of a subject (chest) resting in a recumbent position on a table top.
Figure 6:
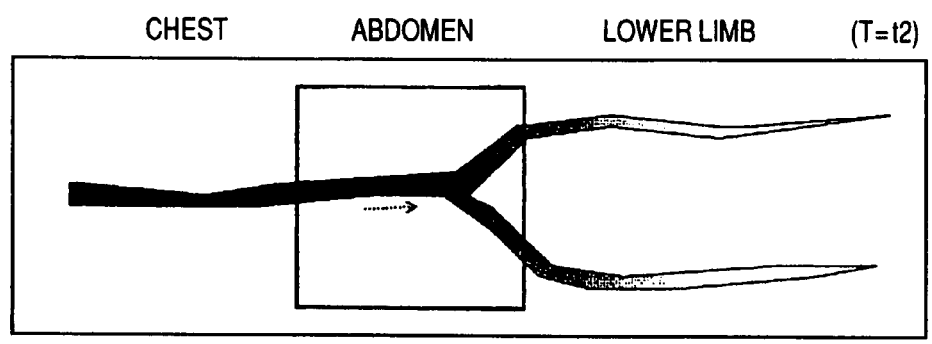
FIG. 6: A figure simulating an angiographic image that is a 2D image of the subject (abdomen) resting in the recumbent position on the table top.
Figure 7:
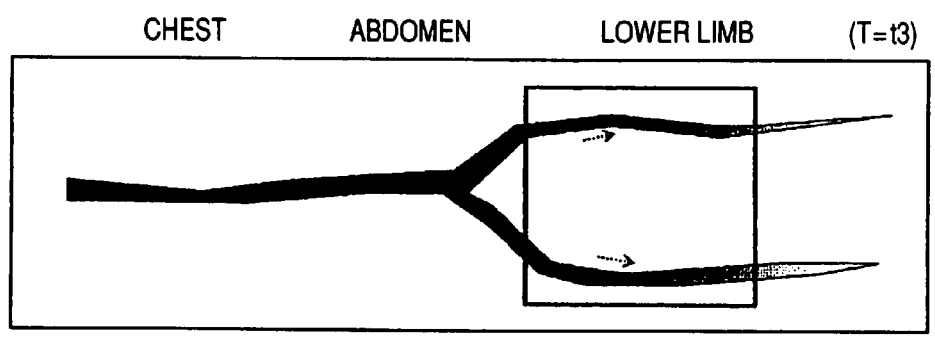
FIG. 7: A figure simulating an angiographic image that is a 2D image of the subject (lower limb) resting in the recumbent position on the table top.

FIGS. 5 to 7 are figures simulating an angiographic image as a 2D image of the subject P resting in a recumbent posture on the table top 35.

FIG. 5 shows an angiographic image of the subject P acquired in a time T of "T=t1" at the step S5. In this angiographic image, the contrast agent moved mainly into the chest, in which case a suitable field-of-view is given in the chest. FIG. 6 shows an angiographic image of the subject P acquired in the later timing "T=t2" than "T=t1" at the step S5. In this angiographic image, the contrast agent moved mainly into the abdomen, in which case a suitable field-of-view is given in the abdomen. Meanwhile, FIG. 7 shows an angiographic image of the subject P reconstructed in the later timing "T=t3" than "T=t2" at the step S5. In this angiographic image, the contrast agent moved mainly into the lower limb, in which case a suitable field-of-view is given in the lower limb.

Figure 8:
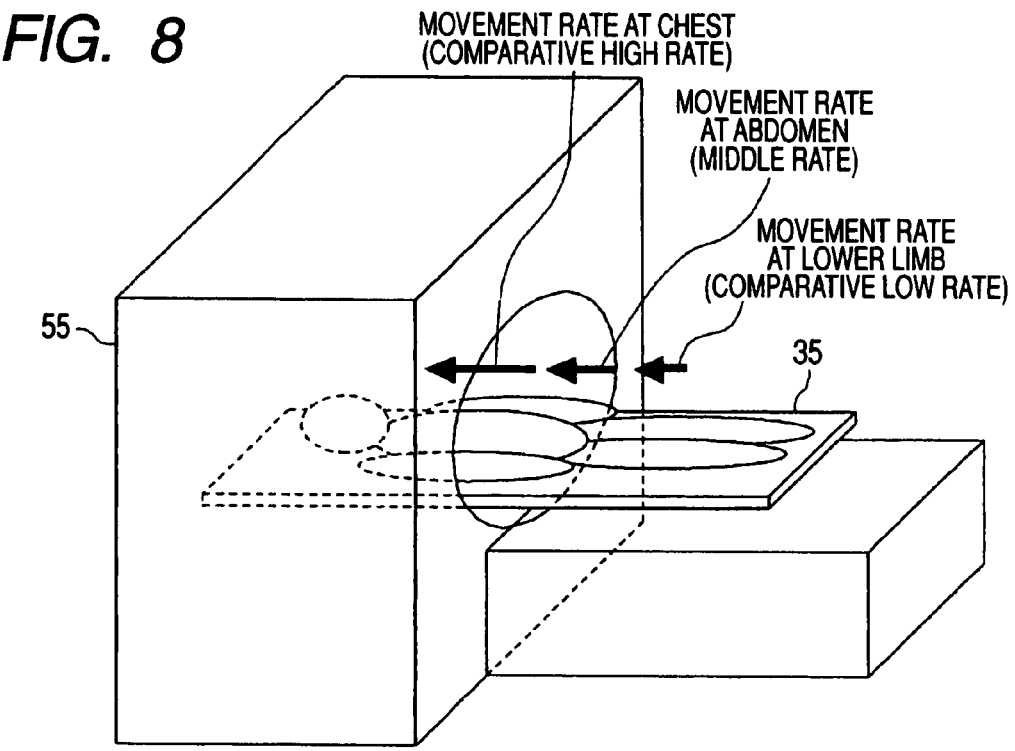
FIG. 8: A figure showing a rate change of the table top.

Meanwhile, the movement rate (blood flow velocity) of the contrast agent is different between the physical regions. The blood flow velocity is the highest in the chest blood vessel and then lower in the abdomen and in the lower limb in this order. Accordingly, in order to take an image in a proper field-ofview for blood flow velocity and reconstruct a proper. 3D image at the step S8, there is a need to move the field-of-view at comparatively high rate at and around the chest, i.e. to move the table top 35 at comparatively high rate, as shown in FIG. 8. There is a need to move the field-of-view at average rate at and around the abdomen, i.e. to move the table top 35 at average rate, as shown in FIG. 8. Meanwhile, there is a need to move the field-of-view at comparatively low rate at and around the lower limb, i.e. to move the table top 35 at comparatively low rate, as shown in FIG. 8.

As shown in FIG. 8, by continuously acquiring 3D raw data at the step S2 while changing the movement rate of the table top 35 into the gantry 55 in the order of comparatively high, average and comparatively low, 3D raw data is continuously acquired by means of the table top 35 whose movement rate is changing. Based thereupon, 2D images can be displayed sequentially at step S6 while proper 3D images can be reconstructed sequentially at the step S8. Incidentally, by repeating the operation of steps S2 to S6 each time 3D raw data is newly acquired at the step S2, the monitor 38 is allowed to display a 2D image, with update, thereon at the step S6.

Figure 9:
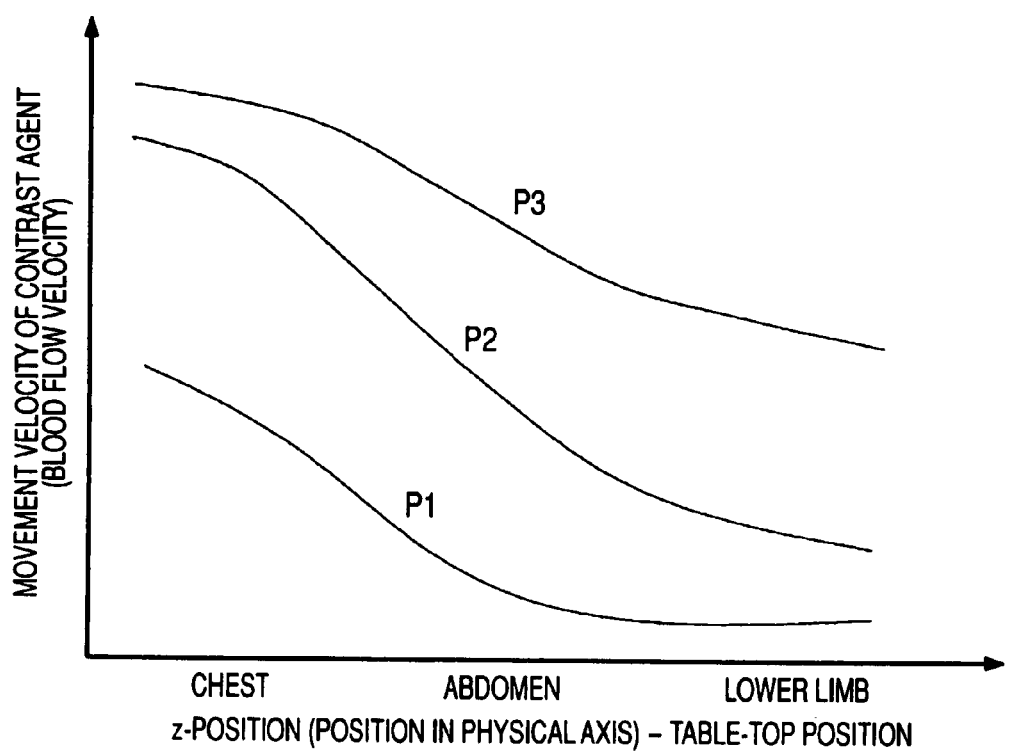
FIG. 9: A graph showing an example of a difference of blood flow velocity on a subject-by-subject basis.

Meanwhile, FIG. 9 is a graph showing an example of a blood flow velocity difference on a subject-by-subject P basis.

FIG. 9 shows a blood flow velocity difference of between an old-aged P1, a middle-aged P2 and a young-aged P3, wherein the blood flow velocity decreases in the direction of from the chest to the lower limb as to the old-aged, middle-aged and young-aged ones P1, P2, P3 (already explained in FIGS. 5 to 7). Meanwhile, there is a tendency that the blood flow velocity wholly is lower in the order of the young-aged one P3, the middle-aged one P2 and the old-aged one P1.

Accordingly, because the blood flow velocity differs on a subject-by-subject basis and from region to region even on the same subject as explained in FIGS. 5, 6, 7 and 9, the movement rate of the table top 35 shown in FIG. 8 cannot be defined in the same way. It is requisite required to change the movement rate of the table top 35 in a manner following the velocity of blood flow differing on a subject-by-subject basis and from region to region even on the same subject.

Therefore, the user is to suitably input a rate-change signal for the table top 35 to the table-top movement-rate control means 102 by use of the input device 39 while viewing a 2D angiographic image displayed on the monitor 38 at the step S6. When taking an image at and around, say, the chest shown in FIG. 5 where blood flow velocity is comparatively high, the field-of-view is moved at comparatively high rate by moving the table top 35 at comparatively high rate. Meanwhile, when taking an image at and around, say, the lower limb shown in FIG. 7 where blood flow velocity is comparatively low, the field-of-view is moved at comparatively low rate by moving the table top 35 at comparatively low rate. For example, the user operates the rate-change-signal input screen by use of the input device 39 and input a rate-change signal for the table top 35 to the table-top movement-rate control means 102.

Figure 10:
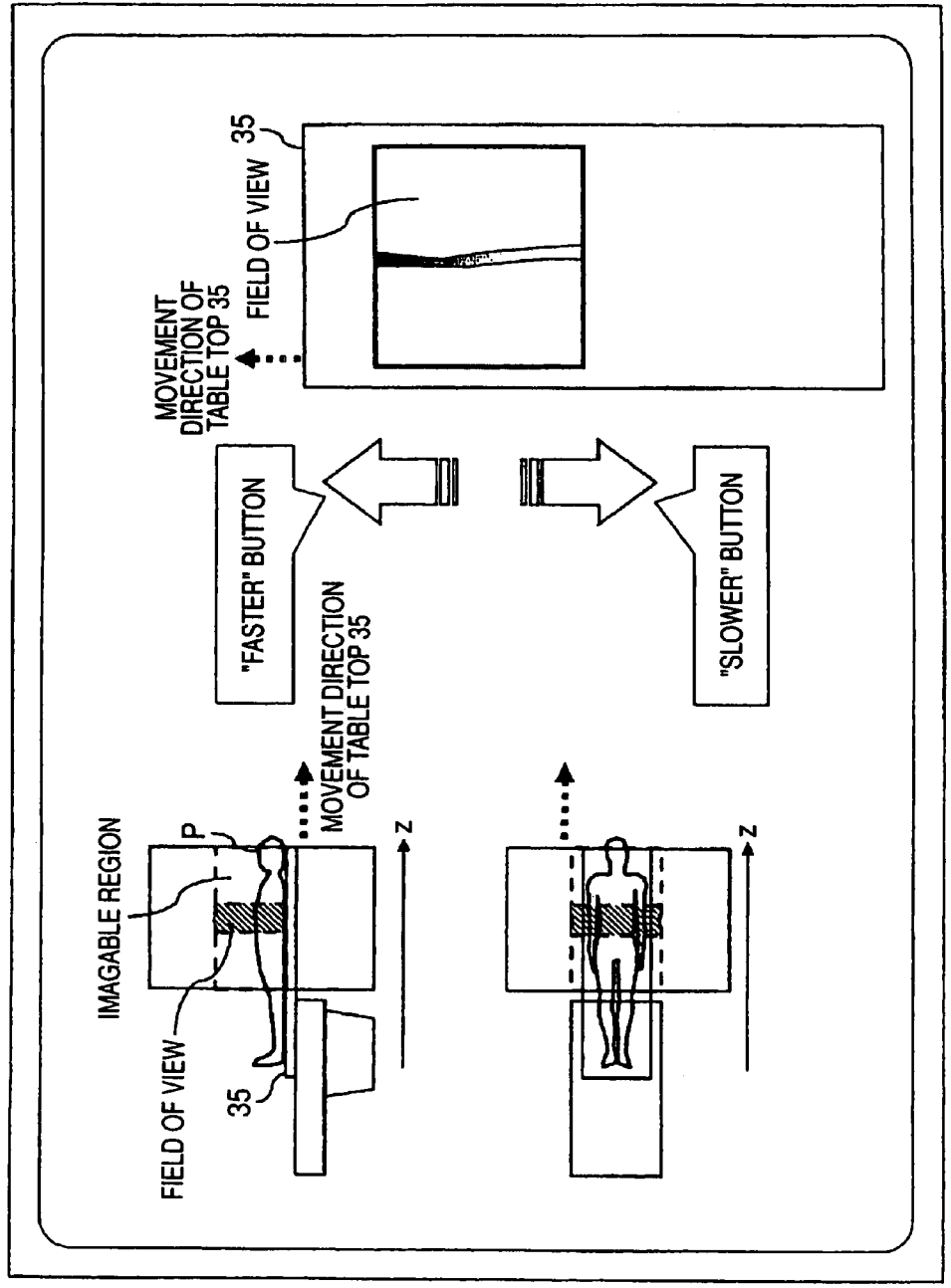
FIG. 10: A figure showing an example of a rate-change signal input screen for the table top.

FIG. 10 is a figure showing an example of a rate-change signal input screen for the table top 35.

FIG. 10 shows a rate-change signal input screen (GUI screen) for the table top 35 that allows the user to operate the input device 39 and input a rate-change signal in desired timing to the computer 32. In the rate-change signal input screen, there are shown as a graphic a positional relationship between the gantry of the magnetic resonance imaging apparatus 10, the table top 35 and the subject P as well as a field-of-view formed by the positional relationship thereof. On the screen, a rate change signal is suitably inputted for the table top 35 of the magnetic resonance imaging apparatus 10.

In the field-of-view graphic at the right side of the rate-change signal input screen, there is displayed in real time as a reference image an angiographic image reconstructed at the step S5 with a movement rate of the table top 35 calculated at the step S13 according to the rate-change signal inputted on the rate-change signal input screen.

The user pushes a "faster" button for blood flow velocity on the rate-change signal input screen when the field-of-view is too slow and a "slower" button when too fast while viewing an angiographic image as a reference image. When the "faster" or "slower" button is pushed, a rate-change signal is inputted to the table-top movement-rate control means 102. Adjusted is a change rate of the table-top 35 figure in the rate-change signal input screen. Furthermore, the table-top movement-rate control means 106 calculates a movement rate of the table top 35 according to the rate-change signal.

Here, shown is the "T=t1" case illustrated in FIG. 5. The user pushes the "faster" button for blood flow velocity, on the rate-change signal input screen while viewing an angiographic image of the chest. When the "faster" button is pushed, the change rate of the table-top 35 graphic is increased on the rate-change signal input screen. Simultaneously, the table-top movement-rate control means 102 calculates a movement rate of the table top 35.

Figure 11:
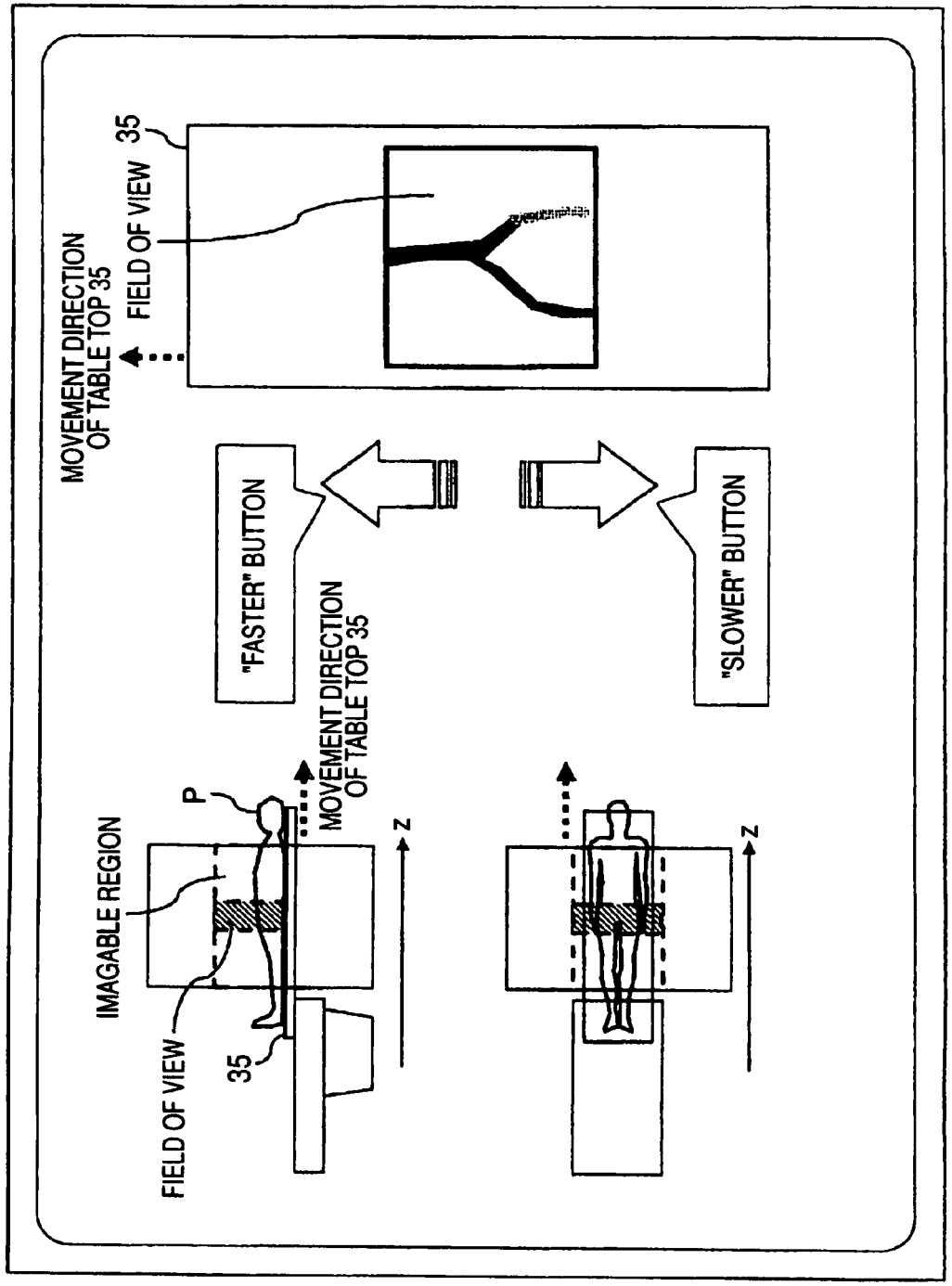
FIG. 11: A figure showing an example of a rate-change signal input screen for the table top.

FIG. 11 is a figure showing an example of a rate-change signal input screen for the table top 35.

The rate-change signal input screen shown in FIG. 11 illustrates the FIG. 6 case. The user pushes a "slower" button for blood flow velocity, on the rate-change signal input screen while viewing an angiographic image of the abdomen. When the "slower" button is pushed, the change rate of the table-top 35 graphic is decreased on the rate-change signal input screen. Simultaneously, the table-top movement-rate control means 102 calculates a movement rate of the table top 35.

Incidentally, the positional relationship figure, on the rate-change signal input screen may be displayed by using the input device 39 depending upon the actual position of the table top 35 measured by a position measuring instrument utilizing a laser, etc.

As explained in FIGS. 10 and 11, by suitably calculating at the step S13 a movement rate of the table top 35 in a manner following the blood flow velocity, onto the HD is recorded a 3D image based on the 3D raw data acquired at the step S2 at the calculated table-top 35 movement rate. Because the 3D image is adapted for the difference of blood flow velocity on a site-by-site basis of the subject P or on a subject-P-by-subject-P basis, it is a proper 3D image to obtain a 3D angiographic image for use in diagnosis.

Incidentally, the angiographic image, as a 3D reconstructed image, may be properly provided by the display control means 107 to the monitor 38 and displayed on the monitor 38.

Figure 12:
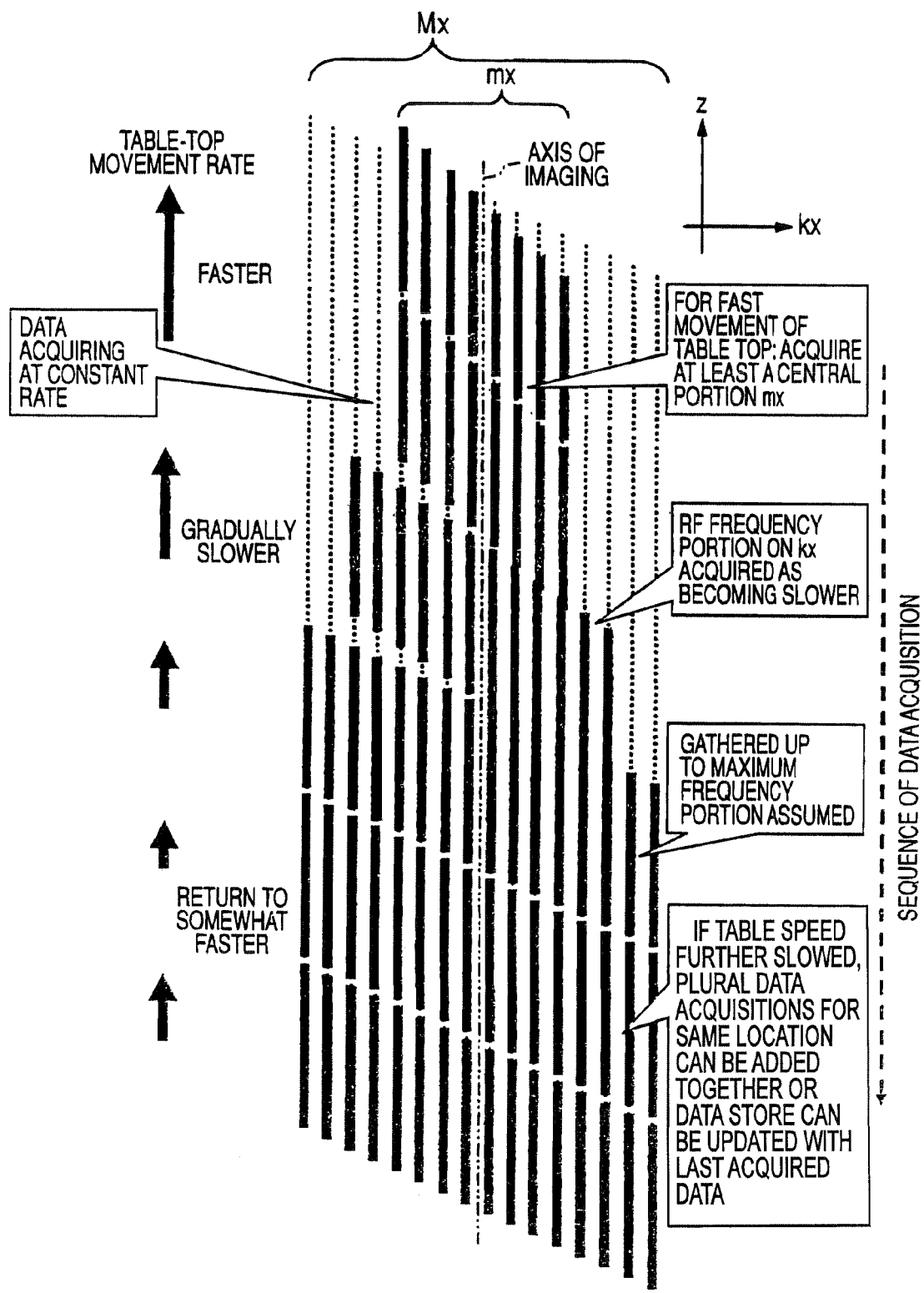
FIG. 12: A figure explaining the sequence of data acquiring units with a movement rate change of the table top.
Figure 13:
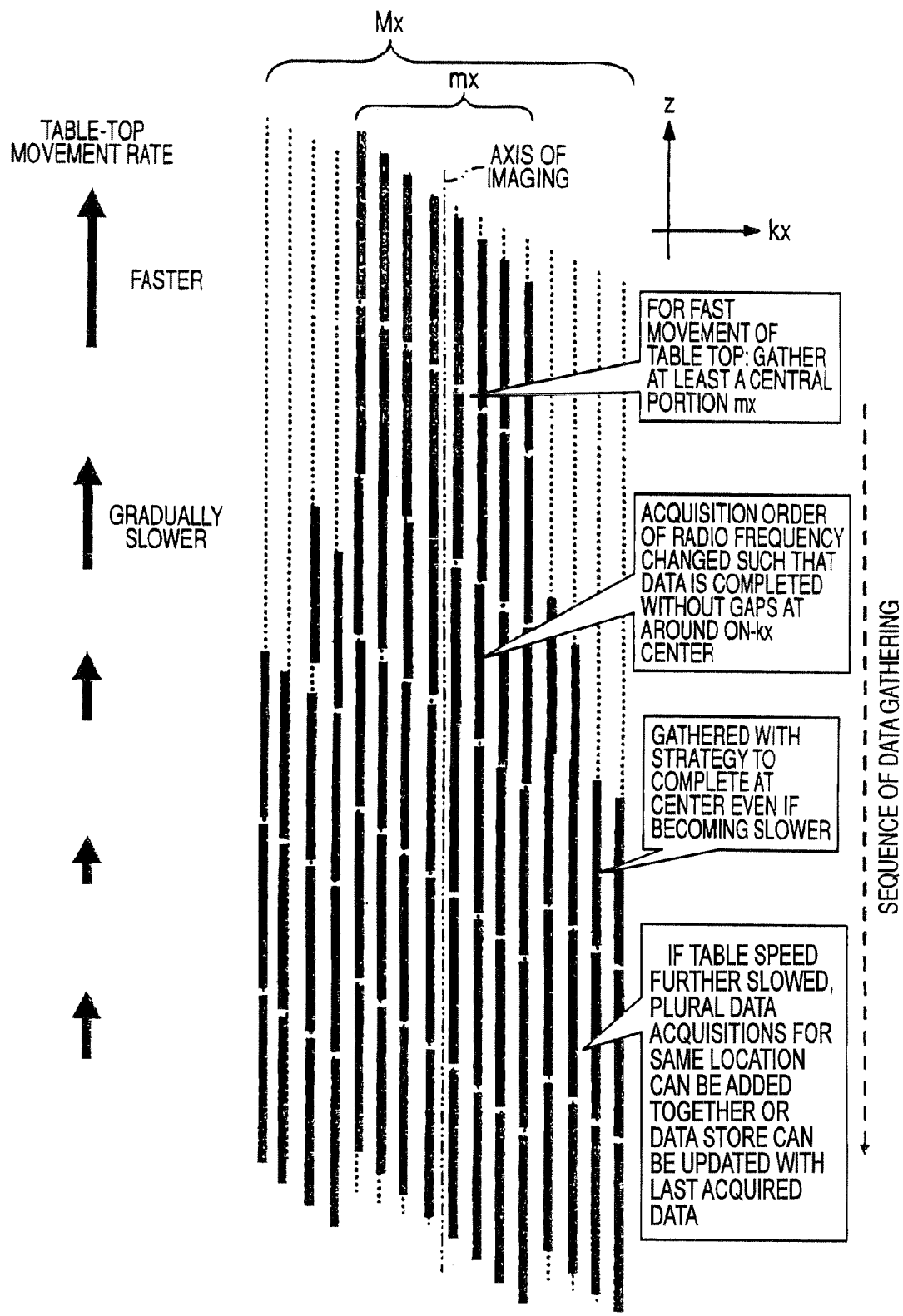
FIG. 13: A figure explaining the sequence of data acquiring units with a movement rate change of the table top.

FIGS. 12 and 13 are figures explaining a data acquiring-unit order in accordance with the movement-rate change of the table top.

On the kx-z hybrid space in FIGS. 12 and 13, data is acquired in the chronological order of from the above (chest) to the below (lower limb) in the figure. The broken line, in the figure, represents a data acquiring unit where the table top moves at constant rate. Meanwhile, the solid line, in the figure, represents a data acquiring unit where a rate-change signal is inputted on the rate-change signal input screen and the movement rate of the table top changes accordingly.

On the kx-z hybrid space shown in FIG. 12, because blood flows at comparatively high rate in a position corresponding to the chest of the subject (the upper in the figure), the table top on which the subject is rested moves at comparatively high rate. Accordingly, in a position corresponding to the chest of the subject on the kx-z hybrid space, data is acquired in a portion mx at least around the axis of imaging.

Next, on the kx-z hybrid space, because the blood flow velocity becomes gradually slower in a region of from the chest to abdomen of the subject (the central in the figure), a rate-change signal is properly inputted on the rate-change signal input screen. As the movement rate of the table top is decreased by the rate-change signal, data is gradually acquired also as to the RF portion of kx in addition to the data collection in the portion mx. Furthermore, when the movement rate of the table top is decreased down to a predetermined velocity by the rate-change signal, data acquiring is up to an assumed portion of the maximum frequency (Mx) as to kx.

Next, on the kx-z hybrid space, because the blood flow velocity in the subject further decreases in a region of from the abdomen to lower limb of the subject (the lower in the figure), a rate-change signal is properly inputted on the rate-change signal input screen. When the movement rate for the table top is decreased down to a predetermined velocity by the rate-change signal, the maximum frequency portion as to kx may be twice acquired for a given location and added together. Otherwise, when the movement rate for the table top is decreased down to a predetermined velocity, the maximum frequency portion as to kx for a multiply sampled location may be updated, e.g., with the last acquired sample (not shown).

Meanwhile, on the kx-z hybrid space shown in FIG. 13, because the blood flows comparatively at high rate in a position corresponding to the chest of the subject (the upper in the figure), the table top on which the subject is rested moves at comparatively high rate. Accordingly, in a position corresponding to the chest of the subject on the kx-z hybrid space, data is acquired in a portion mx at least around the axis of imaging.

Next, on the kx-z hybrid space, because the blood flow velocity becomes gradually slower in a region of from the chest to abdomen of the subject (the central in the figure), a rate-change signal is properly inputted on the rate-change signal input screen. As the movement rate of the table top is decreased by the rate-change signal, data is acquired as to the RF portion of kx by changing the acquisition order of RF portion of kx in a manner completing the data without omission at around the axis-of-imaging kx in addition to the acquiring as to the portion mx. Furthermore, when the movement rate of the table top is decreased down to a predetermined velocity by the rate-change signal, acquiring is with a strategy for completion at around the axis of imaging.

Next, on the kx-z hybrid space, because the blood flow velocity in the subject further decreases in a region of from the abdomen to lower limb of the subject (the lower in the figure), a rate-change signal is properly inputted on the rate-change signal input screen. When the movement rate of the table top is decreased by the rate-change signal, the maximum frequency portion (Mx) of kx may be twice acquired for a given location and added together. Otherwise, when the movement rate of the table top is decreased down to a predetermined velocity, the maximum frequency portion (Mx) of kx for a multiply sampled location may be updated, e.g., with the last acquired sample (not shown).

Figure 14:
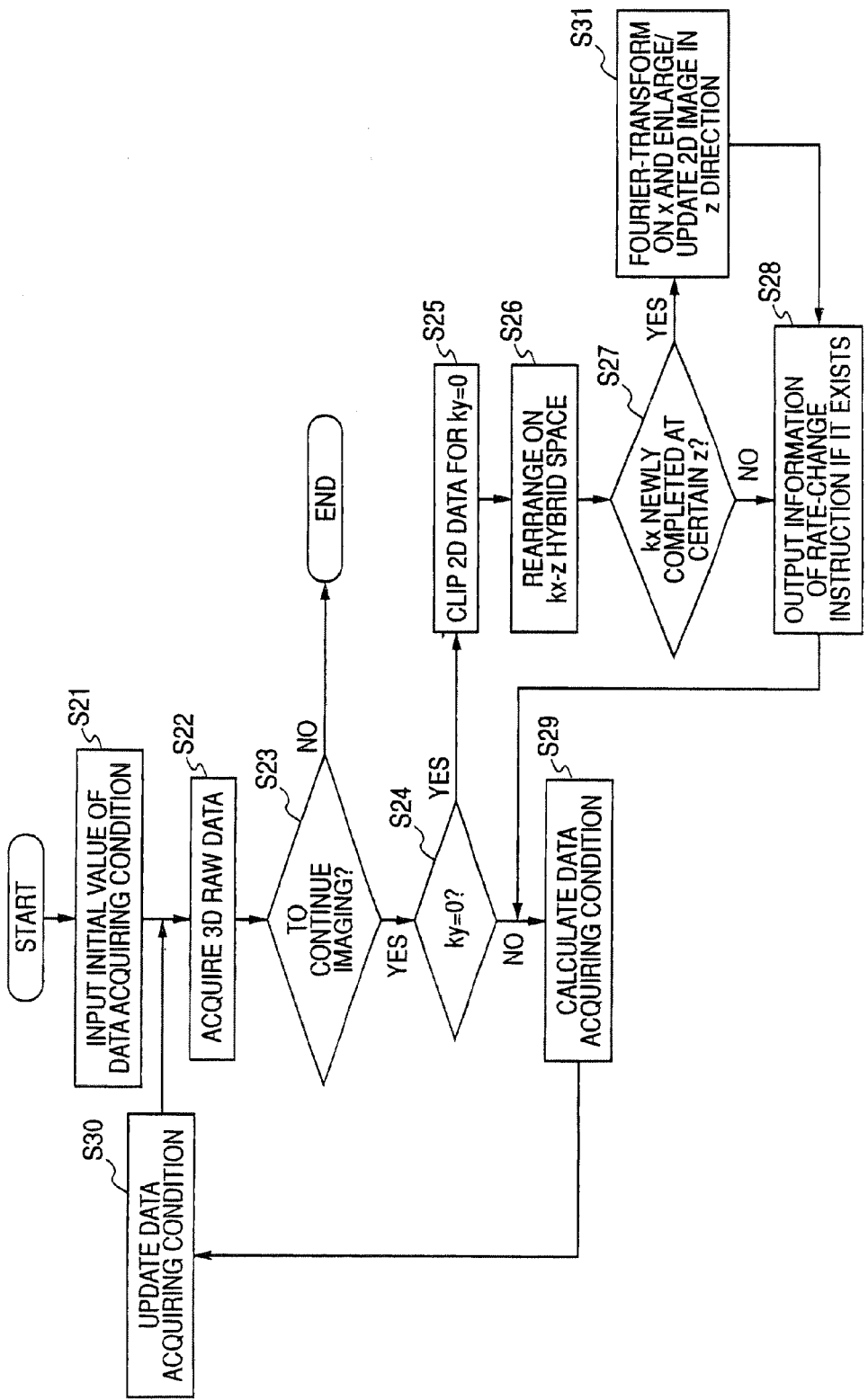
FIG. 14: A flowchart showing a modification to the magnetic resonance angiography method according to the invention.

FIG. 14 is a flowchart showing a modification to the magnetic resonance angiography method according to the invention.

According to the modification to the magnetic resonance angiography method, the initial value of data acquiring condition is inputted to the computer 32 by the user using the input device 39 (step S21). The data acquiring condition includes the movement rate of the table top 35 and the position of the table top 35 on the kx-ky-z hybrid space.

The data acquiring means 103 acquires 3D raw data at a movement rate and position of the table top 35 under a data-acquiring condition inputted (step S22) Concurrently with the acquiring of 3D raw data at the step S22, determination is made as to whether or not to continue the imaging of the subject P depending upon whether or not required data was completed based upon the data acquired (step S23).

When determined Yes at the step S23, i.e. when determined to continue the imaging of subject P, determination is made as to whether or not "ky=constant", e.g. "ky=0" (step S24).

When determined Yes at the step S24, i.e. when determined as "ky=0", 2D data for "ky=0" is extracted by the 2D-data extract means 104a concurrently with the acquiring of 3D raw data at the step S22 (step S25), and then Fourier-transformed in the z-axis direction by the 2D-data rearranging means 105 into a rearrangement on the kx-z hybrid space (step S26). Then, determination is made at the step S26 on the z-data completed in the kx direction, as to whether or not kx was newly completed on a certain z-coordinate (step S27). When determined No at the step S27, i.e. determined that kx was not newly completed as to the certain z-coordinate, if there is a rate-change instruction, the information thereof is outputted (step S28).

The table-top movement-rate control means 102 calculates a data acquiring condition, i.e. a post-change movement rate of the table top 35 and a next position of the table top 35, by totalizing the 3D raw data already acquired under the data acquiring condition inputted at the step S1 and the rate-change signal, concurrently with the acquiring of 3D raw data at the step S22 (step S29). Then, the data acquiring condition inputted at the step S1 is updated to the data acquiring condition calculated at the step S24 (step S30), to acquire again 3D raw data under the data acquiring condition calculated at the step S24 (step S22).

Meanwhile, when determined Yes at the step S27, i.e. when determined that kx was newly completed on a certain z-coordinate, Fourier-transform is performed in the x-axis direction, to update the 2D image with an enlargement in the z-axis direction (step S31) wherein, if there is a rate-change instruction, the information thereof is outputted (step S28). By displaying the 2D image updated at the step S31 on the monitor 28, the user inputs a rate-change signal.

Meanwhile, when determined No at the step S23, i.e. when determined not to continue the imaging, the imaging of the subject P is terminated.

Meanwhile, when determined No at the step S24, i.e. when not "ky=0", a data acquiring condition is calculated (step S29).

Incidentally, in the exemplary embodiments, a known gradient magnetic-field linearity correction technique may be applied because, as the field-of-view is distant greater from the axis of imaging thereof, linearity (gradient magnetic-field inclination) generally worsens to distort the form of an FT-processed MR image.

In addition, the projection processing in the exemplary embodiments is to obtain a projection image of a blood vessel on the basis of the TWIP (twisted projection) scheme that is applied with a phase twist technique to suppress against the signals of from a stationary region other than a fluid region, in order to emphasize the angiographic image. In the post-processing of 3D image data, the scheme may be conformed that provides a "twist effect" due to a so-called "twister".

Furthermore, on the kz-x hybrid space is applied with a 3D-TRICKS (time-resolved imaging of contrast kinetics)

technique as a sampling scheme with scanning by setting up an order of acquiring units (excitations) in a pulse sequence such that acquiring is greater in amount as to the data arranged at around the axis of imaging than the data arranged in the other regions on the k space. This can further improve the temporal resolution.

According to the exemplary magnetic resonance imaging apparatus 10 and magnetic resonance angiography method, the movement rate of the table top 35 can be controlled while observing the actual blood flow velocity interior of a subject, thus obtaining proper image data following the blood flow velocity that is different on a subject-by-subject basis or on a site-by-site basis even in the same subject.

What is claimed is:

1. A magnetic resonance imaging apparatus having a table-top for resting a subject thereon, a table-top drive mechanism for moving the table-top in a lengthwise direction (z-axis direction), and a computer for controlling a movement rate of the table-top by providing a control signal to the table-top drive mechanism, so that a 2D real-time monitor image is produced during a continuous table-top movement 3D imaging process, the apparatus comprising:
    a table-top movement-rate control unit configured to control the table-top drive mechanism to move the table-top;
    a data collecting unit configured to collect raw 3D data in kx, ky, and kz space provided by a nuclear magnetic resonance signal while moving the table-top where x and y coordinate axes are orthogonal to said z-axis;
    a 2D-image acquiring unit configured to acquire a 2D monitor image based upon raw 2D data forming a part of the raw collected 3D data, concurrently with collection of the raw 3D data; and
    a display control unit configured to control display of the 2D monitor image, concurrently with ongoing collection of the raw 3D data;
    wherein the 2D-image acquiring unit has
        a 2D-data acquiring unit configured to extract raw 2D data, related to k-space y-axis position ky where ky is constant, out of the collected raw 3D data,
        a 2D-data rearranging unit configured (a) to Fourier-transform in a z-axis direction the extracted raw 2D data of the collected raw 3D data, (b) not to Fourier-transform remaining collected raw 3D data, and (c) to place the extracted raw 2D data transformed in the z-axis direction onto a kx-z hybrid space, and
        a 2D-image reconstructing unit configured to perform a one-dimensional Fourier transform on z-data completed in a kx direction on the placed extracted raw 2D-data to acquire a 2D monitor image for real space, thereby enhancing timeliness of the displayed monitor image by reducing the amount of data processing time required to produce the monitor image during concurrent acquisition of the raw 3D data.

2. A magnetic resonance imaging apparatus according to claim 1, further comprising:
    a 3D-image acquiring unit configured to acquire a 3D image based upon the collected raw 3D data,
    wherein the table-top movement-rate control unit is configured to calculate the movement rate according to a rate-change signal inputted to move the table-top at the movement rate calculated.

3. A magnetic resonance imaging apparatus according to claim 1, wherein ky=0.

4. A magnetic resonance imaging apparatus according to claim 1, wherein said apparatus includes an RF coil made as a multi-coil structured with a plurality of surface coils at least in a z direction, to simultaneously receive the nuclear magnetic resonance signal at the plurality of surface coils.

5. A magnetic resonance imaging apparatus according to claim 2, wherein the 3D-image acquiring unit includes a 3D-data rearranging unit configured to Fourier-transform in the z-axis direction the collected raw 3D data and to rearrange the same on a kx-ky-z hybrid space, a 3D-image reconstructing unit configured to perform a two-dimensional Fourier transform on the z-data completed in a kx/ky direction by the 3D-data rearranging unit and to acquire a 3D image for real space, and a 3D-image processing unit configured to perform image processing on the acquired 3D image.

6. A magnetic resonance imaging apparatus according to claim 2, further comprising:
    an input unit configured to input the rate-change signal to the table-top movement-rate control unit.

7. A magnetic resonance imaging apparatus according to claim 2, further comprising:
    a position measuring unit configured to measure an actual position of the table-top.

8. A magnetic resonance imaging apparatus having a table-top for resting a subject thereon, a table-top drive mechanism for moving the table-top, and a computer for controlling a movement rate of the table-top by providing a control signal to the table-top drive mechanism, so that a 2D real-time monitor image is produced during a continuous table-top movement 3D imaging process after a contrast agent is injected to a blood vessel interior of the subject, thereby imaging temporal movement of the contrast agent, the apparatus comprising:
    a data collecting unit configured to collect raw 3D data in kx, ky, and kz space provided by a nuclear magnetic resonance signal including a signal in which blood flow of the subject is emphasized while moving the table-top where x and y coordinate axes are orthogonal to said z-axis;
    a 2D-image acquiring unit configured to acquire a 2D monitor image based upon raw 2D data forming a part of the collected raw 3D data, concurrently with collection of the raw 3D data;
    a display control unit configured to control display of the 2D monitor image, concurrently with ongoing collection of the raw 3D data;
    a 3D-image acquiring unit configured to acquire a 3D image based upon the 3D data; and
    a table-top movement-rate control unit configured to calculate the movement rate according to an inputted rate-change signal and to move the table-top at the movement rate calculated, concurrently with collection of the raw 3D data;
    wherein the 2D-image acquiring unit has
        a 2D-data acquiring unit configured to extract raw 2D data, related to k-space y-axis position ky where ky is constant, out of the collected raw 3D data,
        a 2D-data rearranging unit configured (a) to Fourier-transform in a z-axis direction the extracted raw 2D data of the collected raw 3D data, (b) not to Fourier-transform remaining collected raw 3D data, and (c) to place the extracted raw 2D data transformed in the z-axis direction onto a kx-z hybrid space, and
        a 2D-image reconstructing unit configured to perform a one-dimensional Fourier transform on z-data of the placed extracted raw 2D data in a kx direction to acquire a 2D monitor image for real space, thereby enhancing timeliness of the displayed monitor image by reducing the amount of data processing time required to produce the monitor image during concurrent acquisition of the raw 3D data.

9. A magnetic resonance angiography method in which a 2D monitor image is produced during a continuous table-top movement 3D imaging process after a contrast agent is injected to a blood vessel interior of a subject, thereby imaging temporal movement of the contrast agent, the method comprising:
- moving the table-top;
- collecting raw 3D data in kx, ky, and kz space provided by a nuclear magnetic resonance signal including a signal wherein blood flow of the subject is emphasized while moving the table-top where x and y coordinate axes are orthogonal to said z-axis;
- acquiring a 2D monitor image based upon raw 2D data forming a part of the collected raw 3D data, concurrently with collection of the raw 3D data;
- displaying the 2D monitor image concurrently with ongoing collection of the raw 3D data;
- acquiring a 3D image based on the raw 3D data; and
- calculating the movement rate according to an inputted rate-change signal, concurrently with collection of the raw 3D data;
- wherein acquiring the 2D-image includes (a) extracting raw 2D data, related to k-space y-axis position ky where ky is constant, out of the collected raw 3D data, (b) Fourier-transforming in a z-axis direction the extracted raw 2D data of the collected raw 3D data, (c) not Fourier-transforming remaining collected raw 3D data, (d) placing the extracted raw 2D data transformed in the z-axis direction onto a kx-z hybrid space, and (e) performing a one-dimensional Fourier transform on z-data completed in a kx direction by said placed extracted raw 2D-data to acquire a 2D monitor image for real space, thereby enhancing timeliness of the displayed monitor image by reducing the amount of data processing time required to produce the monitor image during concurrent acquisition of the raw 3D data; and
- moving the table-top at the movement rate calculated.

10. A magnetic resonance angiography method according to claim 9, wherein the ky=0.

11. A magnetic resonance angiography method according to claim 9, wherein the z-data completed in the kx direction at the 2D-data rearranging step, when kx is newly completed on a predetermined z coordinate, is Fourier-transformed in x-axis direction to thereby enlarge the 2D monitor image in the z-axis direction.

12. A magnetic resonance angiography method according to claim 9, wherein applied is a TRICKS (time-resolved imaging of contrast kinetics) technique as a sampling scheme for scanning by setting up an order of collecting units in a pulse sequence such that collecting is greater in amount as to the data arranged at and around the axis of imaging than data arranged in other regions in the kx-z hybrid space.

13. A magnetic resonance angiography method according to claim 9, wherein the 3D-image acquiring step has a 3D-data rearranging step that Fourier-transforms in the z-axis direction the raw 3D data and rearranges the same on a kx-ky-z hybrid space, a 3D-image reconstructing step that performs a two-dimensional Fourier transform on the z-data completed in a kx/ky direction at the 3D-data rearranging step and acquires a 3D image for a real space, and a 3D-image processing step that performs an image processing on the 3D image acquired at the 3D-image acquiring step.

14. A magnetic resonance angiography method according to claim 13, wherein the 3D-image processing step performs an SVR (shaded volume rendering) processing, a MaxIP (maximum intensity projection) processing, a MinIP (minimum intensity projection) processing or an MPR (multiple plane rendering) processing, on the 3D image acquired at the 3D-image reconstructing step.

15. A magnetic resonance angiography method according to claim 9, further comprising:
- a 3D-image recording step that records the 3D-image acquired at the 3D-image acquiring step.

16. A magnetic resonance angiography method according to claim 9, wherein a post-change movement rate and next position of the table-top is calculated by totalizing the raw 3D data already collected with a rate-change signal.

17. A magnetic resonance angiography method according to claim 9, wherein the nuclear magnetic resonance signal is received simultaneously at a plurality of surface coils at least in a z-axis direction, to reconstruct the 2D monitor image or the 3D image based on raw 3D data constituted by the nuclear magnetic resonance signal.

18. A magnetic resonance angiography method according to claim 9, wherein applied with a gradient magnetic-field non-linearity correction technique that corrects for linearity in a field of view.

19. A magnetic resonance angiography method according to claim 9, wherein applied with a TWIP (twisted projection) method making use of a phase twisted technique to suppress against a signal emanating from stationary regions interior of the subject not constituting flowing fluid.

20. A magnetic resonance angiography method comprising:
- moving in a z-axis direction a table-top for resting a subject thereon;
- collecting data using a magnetic resonance excitation in a 3D region of the subject while continuously moving the table-top and collecting raw 3D data in kx, ky, and kz space provided by a 3D nuclear magnetic resonance signal from the 3D region;
- acquiring 2D-image data forming a part of the collected raw 3D data, concurrently with collection of the raw 3D data;
- producing a 2D monitor image based on the raw 2D data, concurrently with collection of the raw 3D data; and
- displaying the 2D monitor image, concurrently with collection of the raw 3D data;
- wherein acquiring the 2D-image includes (a) extracting raw 2D data, related to k-space y-axis position ky where ky is constant, out of the collected raw 3D data, (b) Fourier-transforming in a z-axis direction the extracted raw 2D data of the collected raw 3D data, (c) not Fourier-transforming remaining collected raw 3D data, (d) placing the extracted raw 2D data transformed in the z-axis direction onto a kx-z hybrid space, and (e) performing a one-dimensional Fourier transform on z-data in a kx direction of the placed extracted raw 2D-data to acquire 2D monitor image for real space, thereby enhancing timeliness of the displayed monitor image by reducing the amount of data processing time required to produce the monitor image during concurrent acquisition of the raw 3D data; and
- each time new 3D data is collected, the 2D-data acquiring step, the 2D-image reconstructing step and the 2D-image display process are repeated to thereby update the displayed 2D monitor image.

* * * * *